United States Patent
Högdahl

(10) Patent No.: US 10,130,775 B2
(45) Date of Patent: Nov. 20, 2018

(54) MEDICAMENT DELIVERY DEVICE

(71) Applicant: Carebay Europe Ltd, Sliema (MT)

(72) Inventor: Stefan Högdahl, Stockholm (SE)

(73) Assignee: Carebay Europe Limited, Sliema, MT (US)

( * ) Notice: Subject to any disclaimer, the term of this patent is extended or adjusted under 35 U.S.C. 154(b) by 230 days.

(21) Appl. No.: 14/915,240

(22) PCT Filed: Aug. 21, 2014

(86) PCT No.: PCT/EP2014/067870
§ 371 (c)(1),
(2) Date: Feb. 28, 2016

(87) PCT Pub. No.: WO2015/028393
PCT Pub. Date: Mar. 5, 2015

(65) Prior Publication Data
US 2016/0213858 A1 Jul. 28, 2016

(30) Foreign Application Priority Data
Aug. 29, 2013 (SE) ...................................... 1350994

(51) Int. Cl.
*A61M 5/32* (2006.01)
*A61M 5/20* (2006.01)
(Continued)

(52) U.S. Cl.
CPC ............ *A61M 5/3202* (2013.01); *A61M 5/20* (2013.01); *A61M 5/2033* (2013.01); *A61M 5/24* (2013.01);
(Continued)

(58) Field of Classification Search
CPC .............. A61M 5/3202; A61M 5/2033; A61M 5/31566
See application file for complete search history.

(56) References Cited

U.S. PATENT DOCUMENTS 4,553,962 A 11/1985 Brunet
5,599,309 A 2/1997 Marshall et al.
(Continued)

FOREIGN PATENT DOCUMENTS

DE 102007032463 A1 1/2009
EP 0114145 A2 7/1984
(Continued)

OTHER PUBLICATIONS

"Definition of Cap", Merriam-Webster, accessed Dec. 8, 2017; https://www.merriam-webster.com/dictionary/cap.*
(Continued)

*Primary Examiner* — Laura Bouchelle
*Assistant Examiner* — Tasnim M Ahmed
(74) *Attorney, Agent, or Firm* — McDonnell Boehnen Hulbert & Berghoff LLP

(57) ABSTRACT

A medicament delivery device includes a housing having distal and proximal ends along a longitudinal axis. The housing is arranged to accommodate a medicament container and a delivery member connected to the container; a reloadable drive mechanism for acting on an accommodated container; a delivery member cover at the proximal end and slidable in relation to the housing along the axis; and a cover lock mechanism that includes a first lock member on an actuator movably arranged in relation to the housing and a second lock member on the cover. The first lock member engages the second lock member to block movement of the cover, and the actuator is movable in relation to the cover such that manually actuating the actuator generally transverse to the axis causes the first lock member to be moved out of engagement with the second lock member, thereby allowing the cover to be moved.

14 Claims, 13 Drawing Sheets

(51) Int. Cl.
    *A61M 5/46*     (2006.01)
    *A61M 5/24*     (2006.01)
    *A61M 5/315*    (2006.01)

(52) U.S. Cl.
    CPC ...... *A61M 5/3158* (2013.01); *A61M 5/31566* (2013.01); *A61M 5/3243* (2013.01); *A61M 5/3257* (2013.01); *A61M 5/46* (2013.01); *A61M 2005/202* (2013.01); *A61M 2005/206* (2013.01); *A61M 2005/208* (2013.01); *A61M 2005/2013* (2013.01); *A61M 2005/2026* (2013.01); *A61M 2005/2073* (2013.01)

(56) References Cited

U.S. PATENT DOCUMENTS

| | | | |
|---|---|---|---|
| 5,865,795 A | | 2/1999 | Schiff et al. |
| 6,203,530 B1 * | | 3/2001 | Stewart, Sr. ........ A61M 5/2033 604/207 |
| 8,070,713 B2 | | 12/2011 | Matusch |
| 2011/0202011 A1 * | | 8/2011 | Wozencroft ........ A61M 5/2033 604/192 |

FOREIGN PATENT DOCUMENTS

| | | |
|---|---|---|
| FR | 1257066 A | 3/1961 |
| WO | 2010/023481 A1 | 3/2010 |

OTHER PUBLICATIONS

"Definition of Surround", Merriam-Webster, accessed Dec. 8, 2017; https://www.merriam-webster.com/dictionary/surround.*
"Definition of Passage", Merriam-Webster, accessed Dec. 8, 2017; https://www.merriam-webster.com/dictionary/passage.*
EPO, Int'l Search Report in PCT/EP2014/067870, dated Nov. 10, 2014.
EPO, Written Opinion in PCT/EP2014/067870, dated Nov. 10, 2014.
English Translation of Description of French Patent Application No. 1257066 dated Mar. 15, 2018.

* cited by examiner

MEDICAMENT DELIVERY DEVICE

TECHNICAL AREA

The present invention relates to a medicament delivery device and in particular to a medicament delivery device arranged with a medicament delivery member cover capable of hiding a medicament delivery member, such as an injection needle, before, during and/or after use.

BACKGROUND OF INVENTION

Reusable auto injectors which can be loaded with a container subassembly, such as a syringe, are known in the prior art. U.S. Pat. No. 5,599,309 discloses an auto injector for use with proprietary syringes. That prior art discloses a device comprising a drive member that receives the rear end of a plunger of a syringe and a trigger for releasing the drive member such that a medicament can be injected. Drawbacks are that the needle is exposed outside the device and visible to the user after the device has been removed from the injection site and that the re-loading is complicated and time consuming.

Further, a number of devices are arranged with medicament delivery member covers that are capable of covering a medicament delivery member, such as an injection needle, before and after a dose delivery.

Some of these devices are arranged with springs that urge the medicament delivery member cover in the proximal direction, and while most devices have a locking function on the medicament delivery member cover after dose delivery, quite a number of devices have their medicament delivery member covers movable before dose delivery after a protective cap or the like has been removed. This increases the risk of accidental injuries because the medicament delivery member cover may be unintentionally pushed in a distal direction, exposing the medicament delivery member. Also if the device is dropped on a hard surface, the medicament delivery member risks being damaged.

The patent application WO 2010/023481 discloses a medicament delivery device provided with a medicament delivery member cover that is lockable before dose delivery. The medicament delivery member cover is held in a locked state by a torsion spring exerting a turning force on the shield in relation to the housing of the device. In order to activate the device a user has to turn the medicament delivery shield against the force of the torsion spring and at the same time press the proximal end of the medicament delivery member cover against a dose delivery site. This operation is not ideal in a user perspective, since it is not intuitive in what direction the shield should be turned and it may be quite awkward to turn the shield when performing e.g. a penetration sequence.

Also, it is not the torsion spring that performs the locking action after the device has been withdrawn from the dose delivery site, but other springs. This is a disadvantage since a common aim when designing medicament delivery devices is to reduce the number of components, and in particular force elements acting inside the device.

There is thus room for improvements for this kind of medicament delivery devices.

BRIEF DESCRIPTION OF INVENTION

As used herein, the term "liquid" encompasses all fluids, solutions, suspensions, emulsions, oils, gels and so forth, which generally behave as liquids at operating temperatures. The term explicitly includes solid compositions dissolved or dispersed in a liquid carrier. Materials behaving as highly viscous liquids are also included.

In the present application, when the term "distal part/end" is used, this refers to the part/end of the medical delivery device, or the parts/ends of the elements thereof, which under use of the device is located the furthest away from the delivery site of the patient. Correspondingly, when the term "proximal part/end" is used, this refers to the part/end of the device, or the parts/ends of the elements thereof, which under use of the device is located closest to the delivery site of the patient.

The aim of the present invention is to remedy the drawbacks of the state of the art devices.

This aim is solved by a medicament delivery device according to the features of the independent claim 1. Preferable embodiments of the invention form the subject of the dependent patent claims.

According to one favourable embodiment, it pertains to a medicament delivery device comprising a generally elongated housing having a distal end and a proximal end along a longitudinal axis (L). The housing may be arranged to accommodate a medicament container and a medicament delivery member connected to the medicament container, and a reloadable drive mechanism capable of, upon activation, acting on said medicament container.

In order to increase safety regarding the medicament delivery member, the device may comprise a medicament delivery member cover operably arranged at the proximal end of the device and slidable in relation to the housing in a longitudinal direction.

According to a favourable solution, the device comprises a medicament delivery member cover lock mechanism, which may comprise a first lock member provided on an actuator that is movably arranged in relation to the housing; and a second lock member provided on said medicament delivery member cover, wherein the first lock member is operably engageable with the second lock member for blocking movement of said medicament delivery member cover and wherein the actuator is movable in relation to the medicament delivery member cover, such that manual actuation of said actuator in a direction generally transversal to the longitudinal axis (L) causes the first lock member to be moved out of engagement with the second lock member of said medicament delivery member cover, thereby allowing said medicament delivery member cover to be moved.

With this solution, the medicament delivery member cover is locked from movement by the medicament delivery member cover lock mechanism. Unintentional injuries due to contact with the medicament delivery member is thereby greatly reduced as well as the risk of the medicament delivery member being damaged if the device is accidentally dropped on a hard surface.

Further, there is an advantage regarding the handling of the device to have the actuator movable in a direction generally transversal to the longitudinal direction, for example using the thumb for unlocking the medicament delivery member cover, instead of being forced to use a whole hand in order to turn a component, especially for patients suffering from reduced dexterity.

According to one preferable embodiment, the first lock member is movable in relation to the actuator and the actuator preferably may comprise a ring-shaped element coaxially surrounding said medicament delivery member cover and arranged movable in a generally radial direction. Thereby a flexible design is obtained in that movement in the generally transversal direction does not interfere with other components and elements inside the housing.

Preferably the actuator may comprise a button attached to said ring-shaped element and protruding through a passage on said housing for manual operation. The actuator is then easily accessible by a user.

In order to keep the first lock member in a locking position until actuation, the medicament delivery member cover lock mechanism may further comprise a first resilient force member operably arranged to urge the actuator in a direction generally transversal to the longitudinal axis (L). The first resilient force element thus ensures that the first lock member is in a locking position with the second lock member until the button has been pressed.

According to a further aspect of the embodiment, the medicament delivery member cover lock mechanism further comprises a second resilient force member operably arranged to urge said first lock member in a direction generally transversal to the longitudinal axis (L).

The first lock member may according to one embodiment comprises a cap arranged to protrude through a first passage on said actuator, and the second lock member on said medicament delivery member cover comprises a second passage in which said cap fits.

Further, the medicament delivery member cover lock mechanism further comprises a first actuation locking member provided on the actuator and; a second actuation locking member provided on the medicament delivery member cover wherein the first actuation locking member is operably engageable to the second actuation locking member for blocking movement of said actuator in a direction generally transversal to the longitudinal axis (L) after the actuator is manually activated whereby said medicament delivery member cover is allowed to be moved. The advantage is that a user can get a visual and tactile indication that the medicament delivery member cover can be actuated or moved/displaced.

According to a further embodiment, the medicament delivery device may comprise a reloadable drive mechanism locking element capable of locking the reloadable drive mechanism in a cocked state, a manually operated release mechanism operably arranged to, upon operation, act on said reloadable drive mechanism locking element for releasing the reloadable drive mechanism, a blocking element operably engageable to the manually operated release mechanism and releasably connected to the medicament delivery member cover, wherein movement of said medicament delivery member cover in a distal direction causes said blocking element to move out of blocking engagement with the manually operated release mechanism, whereby said release mechanism is free to be manually operated for activating dose delivery. With this solution, safety is increased in that it further comprises a release mechanism for the reloadable drive mechanism. However, the release mechanism may not be operated until the medicament delivery shield lock mechanism has been activated. Thus, a two-step operation is necessary for providing a dose of medicament from the device. This ensures that the risk of activating the device unintentionally is greatly reduced.

According to a further aspect of the embodiment, the release mechanism may comprise a trigger button operably arranged on said housing and configured to interact with the reloadable drive mechanism. Again, such a solution is easy to handle and intuitive for a user.

According to another embodiment, the medicament delivery device may further comprise a reloadable drive mechanism capable of, upon activation, act on said medicament container for expelling a dose of medicament, a reloadable drive mechanism locking element capable of locking said reloadable drive mechanism in a cocked state, a release mechanism operably arranged to, upon operation, act on said reloadable drive mechanism locking element for releasing said reloadable drive mechanism, wherein movement of said medicament delivery member cover in a distal direction causes said release mechanism to act on said reloadable drive mechanism locking element for activating dose delivery.

According to another aspect of the two embodiments, the reloadable drive mechanism comprises a plunger rod driver arranged axially moveable within the housing between a distal end position and a proximal end position, and a drive spring configured to bias the plunger rod driver towards its proximal end position and wherein the reloadable drive mechanism locking element is configured to interact with the plunger rod driver to hold the plunger rod driver with the drive spring in the distal position.

According to another aspect of the two embodiments, the plunger rod driver and the drive spring are configured to act on a plunger rod which is connected to a stopper positioned inside the medicament container.

With this solution there is one safety feature, which is the medicament delivery member lock mechanism and when the medicament delivery member cover is released, its movement in the distal direction, when pressing the device against a dose delivery site, will cause an activation of the device and thus a dose delivery. This solution may be adequate when a lower degree of safety is desired.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
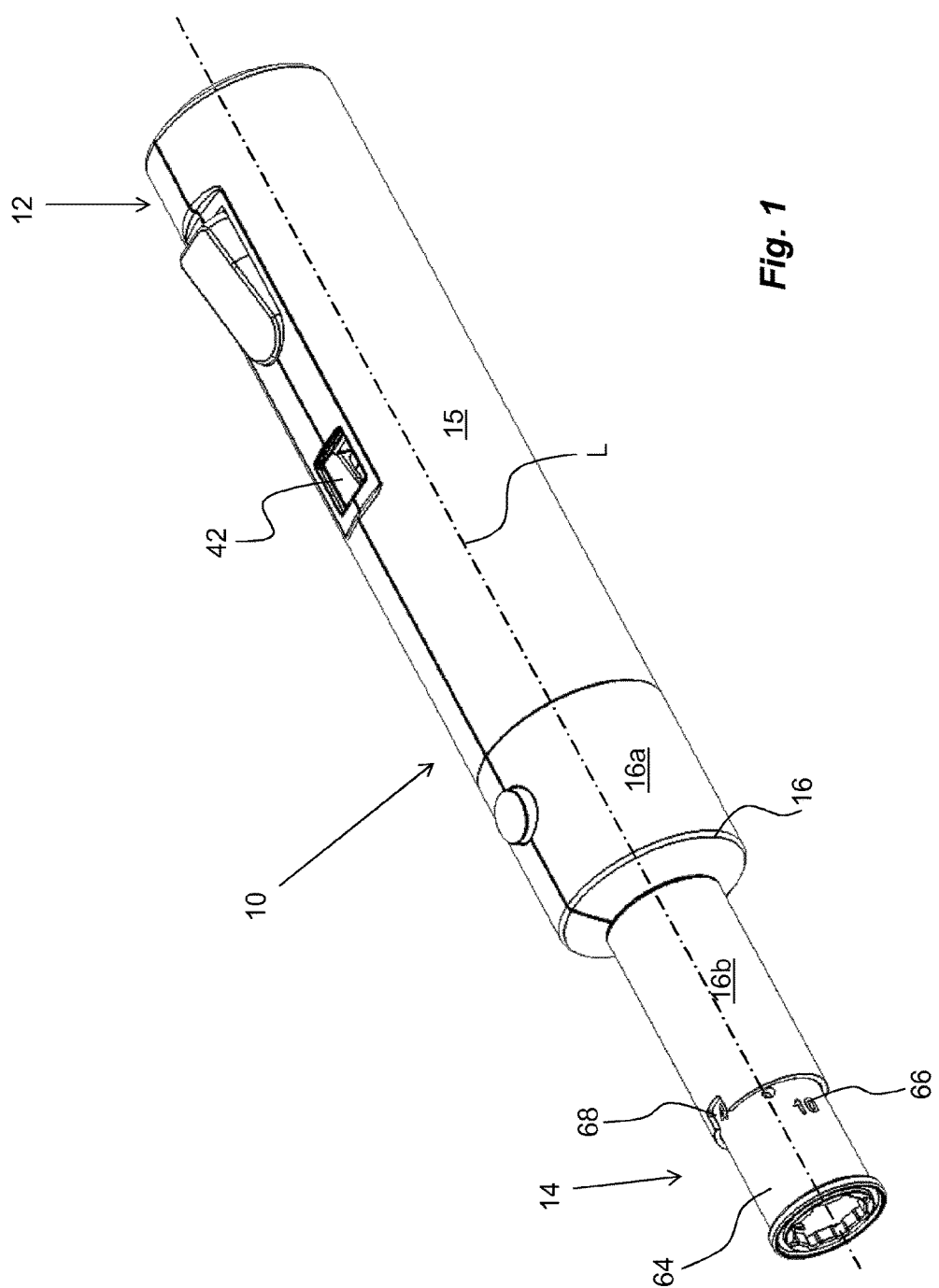
FIG. 1 is a perspective view of an embodiment of the present invention.
Figure 2:
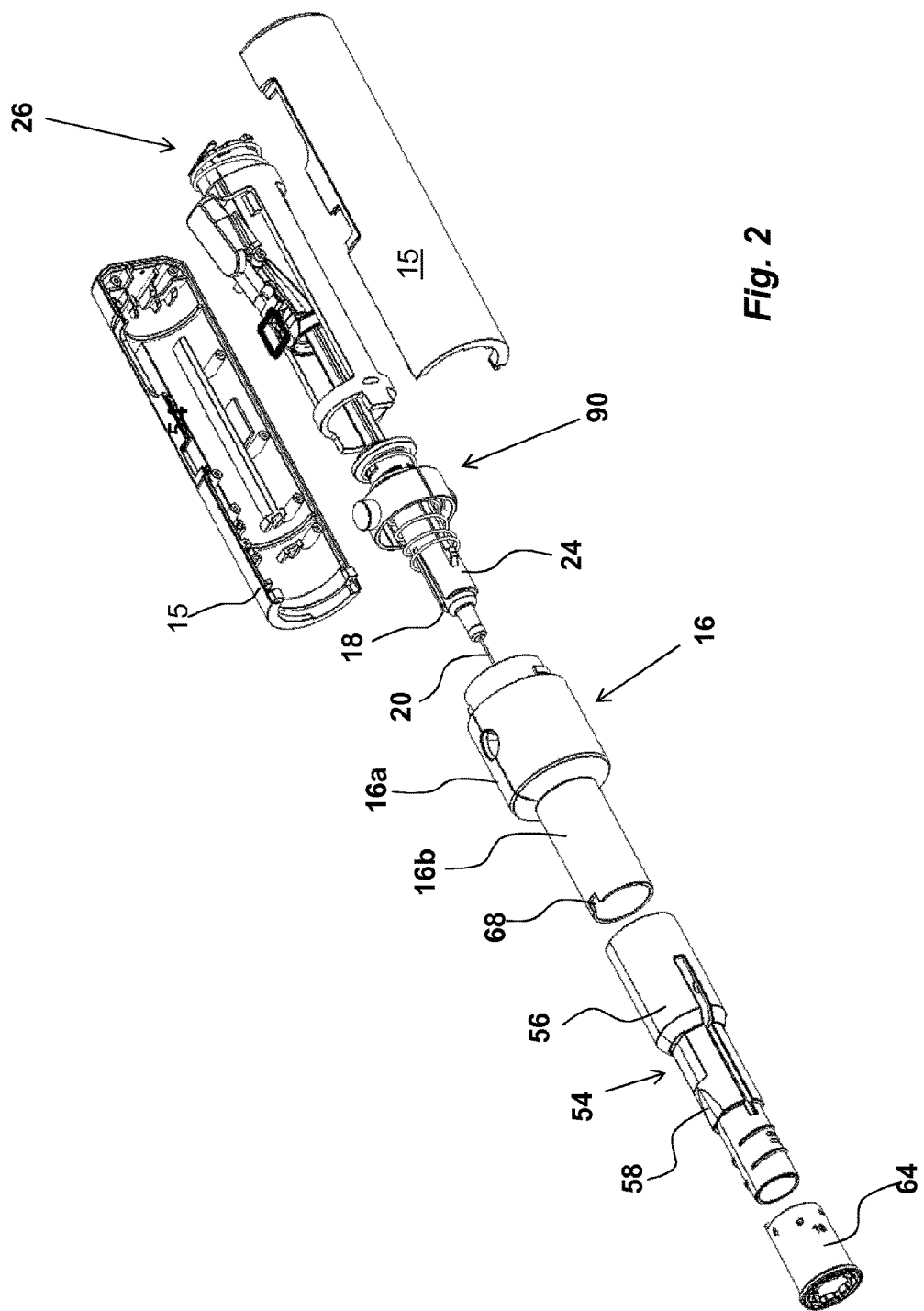
FIG. 2 is an exploded view of the embodiment of FIG. 1.

The embodiment shown in the drawings comprises a generally elongated main housing 10 having a distal end 12 and a proximal end 14 along a longitudinal axis (L), FIG. 1. In the present embodiment, the housing 10 is divided in two parts. At the proximal end 14 a proximal housing part 16 is arranged to be releasibly attached to a distal housing part 15. The proximal housing part 16 comprises a first tubular part 16*a* having generally the same diameter as the distal housing part 15 and a second tubular part 16*b* having a lesser diameter than the first tubular part 16*a*. Attaching elements could comprise threads, bayonet connections, snap-in elements and the like. The proximal housing part 16 is designed to accommodate a medicament container 18 enclosing a medicament, FIG. 2. An appropriate medicament delivery member 20, FIG. 2, is attached to, or made integral with the medicament container. A movable stopper 22 is further arranged inside the medicament container, FIG. 3. The medicament container 18 is preferably a syringe having an elongated plunger rod 30 which is connected to the stopper 22. The medicament container 18 is preferably arranged in a medicament container holder 24, FIGS. 2 and 3. The medicament container holder 24 is arranged to be slidable in the longitudinal direction as will be explained below.

Figure 3:
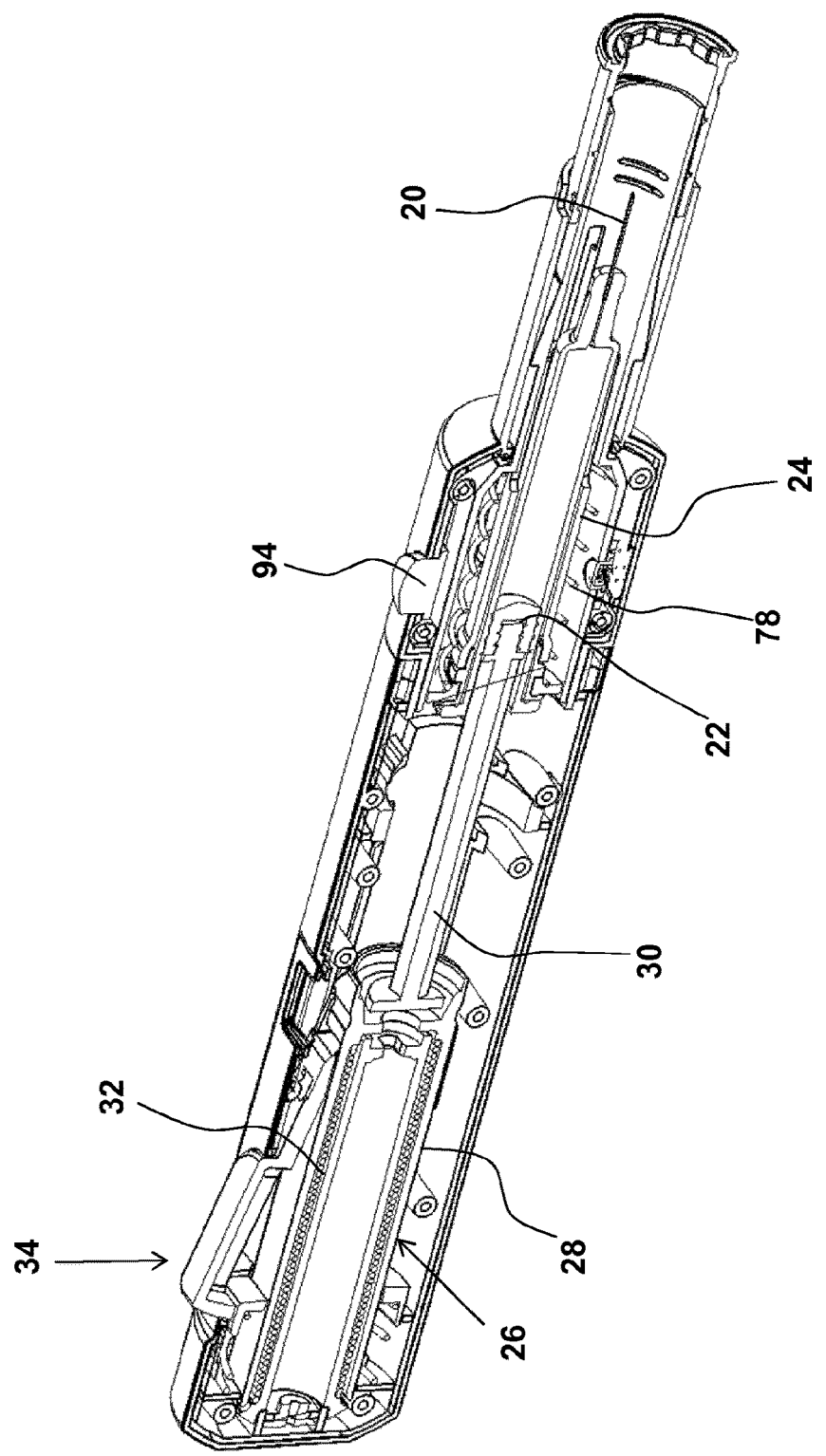
FIG. 3 is a cross-sectional view of the embodiment of FIG. 1, FIGS. 4-8 are detailed view of different components of the embodiment of FIG. 1, FIGS. 9-11 are cross-sectional views of the embodiment of FIG. 1 in different functional states.

The device further comprises a reloadable drive mechanism 26 arranged in the distal housing part 15. The reloadable drive mechanism 26 comprises a plunger rod driver 28 arranged axially moveable within the housing 10 between a distal end position as seen in FIG. 3, and a proximal end position. The proximal end of the plunger rod driver 28 is in contact with the distal end of the elongated plunger rod 30. The proximal end position of the plunger rod driver 28 corresponds to a position where the plunger rod 30 and the stopper 22 have been pressed to the end of the stroke of the plunger rod 30, i.e. the medicament container 18 has been emptied, and the distal end position of the plunger rod driver 28 corresponds to a position where the plunger rod 30 and the stopper 22 have not yet been moved, i.e. the medicament container 18 is full.

Figure 4:
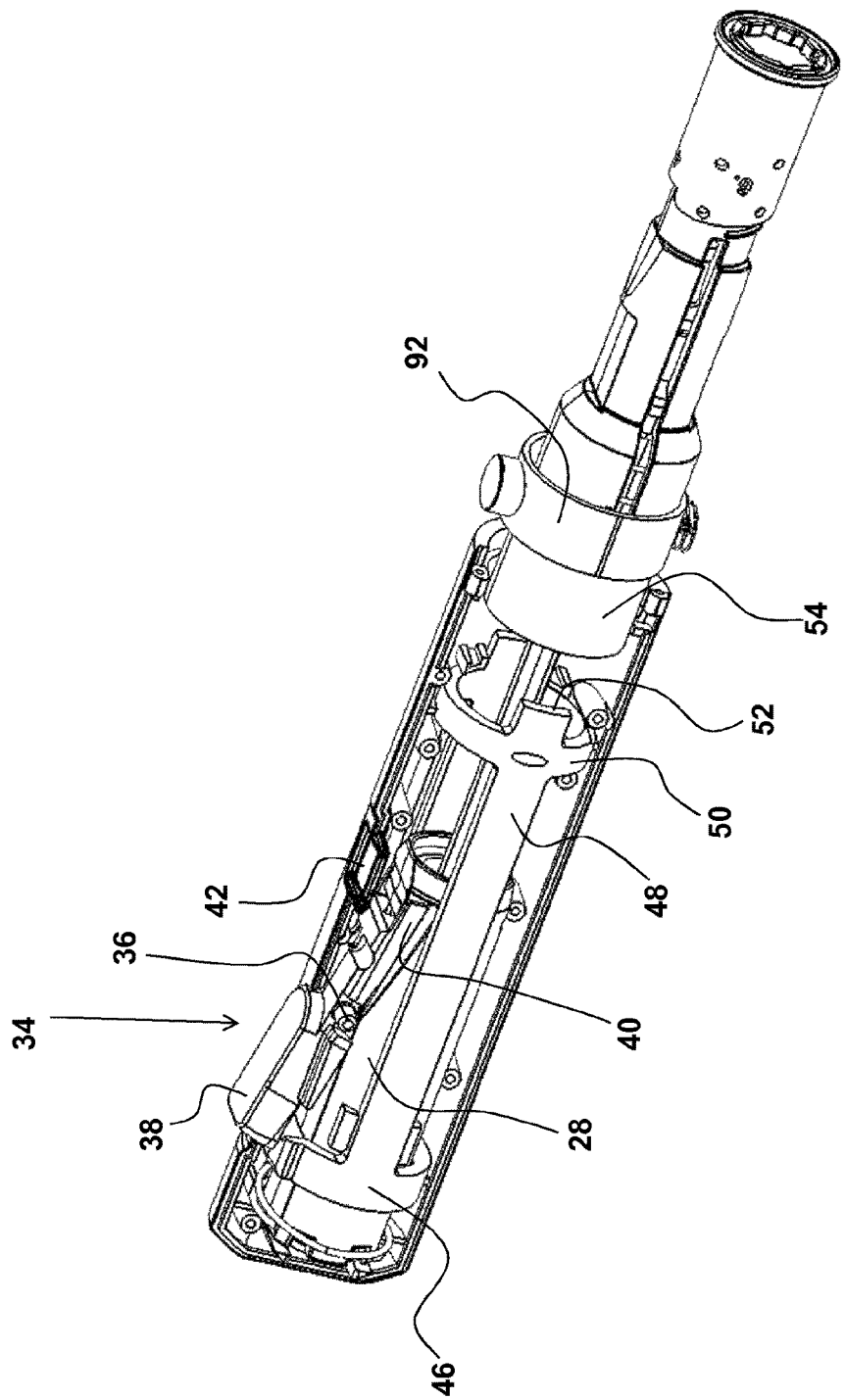

The reloadable drive mechanism 26 further comprises a drive spring 32, preferably a helical coil spring, which biases the plunger rod driver 28 towards its proximal end position. A manually operated release mechanism 34 for releasing the plunger rod driver 28 of the reloadable drive mechanism 26 from the distal, or cocked, position to the proximal, or extended, position is arranged at an outer surface of the housing 10. The release mechanism 34 is pivotable around a pivoting axle 36, FIG. 4, between an undepressed position and a depressed position and comprises a trigger button 38, which operably acts on a reloadable drive mechanism locking element 40 which locks and interacts with the plunger rod driver 28 to hold the plunger rod driver 28 and the drive spring 32 in the distal or cocked position. Thus, the reloadable drive mechanism locking element is configured to lock said reloadable drive mechanism 26 in a cocked state.

Adjacent, or at least near, the release mechanism 34 a status window 42 is arranged through which symbols provided on the plunger rod driver 28 are visible to indicate the status of the medicament delivery device. The status window 42 is preferably made of a transparent, or at least translucent, plastic material.

Further, a blocking element 46 is arranged to operatively act on the release mechanism 34 for preventing actuation of the release mechanism in a first position and to allow actuation of the release mechanism in a second position. The blocking element 46 is arranged surrounding the plunger rod driver 28 and is in an initial position positioned distally of the release mechanism 34 such that a part of the first blocking element 46 is under the distal end of the push button 38 as seen in a radial direction (i.e. radially inside the push button), FIG. 4. In this position, the push button 38 is prevented form pivoting around the pivoting axle 36, thus preventing the activation of the device.

The blocking element 46 is arranged with two elongated arms 48, which arms are inter-connected by a proximal ring-shaped second element 50. The arms 48 end in proximally directed end surfaces 52, FIG. 4.

Figure 5:
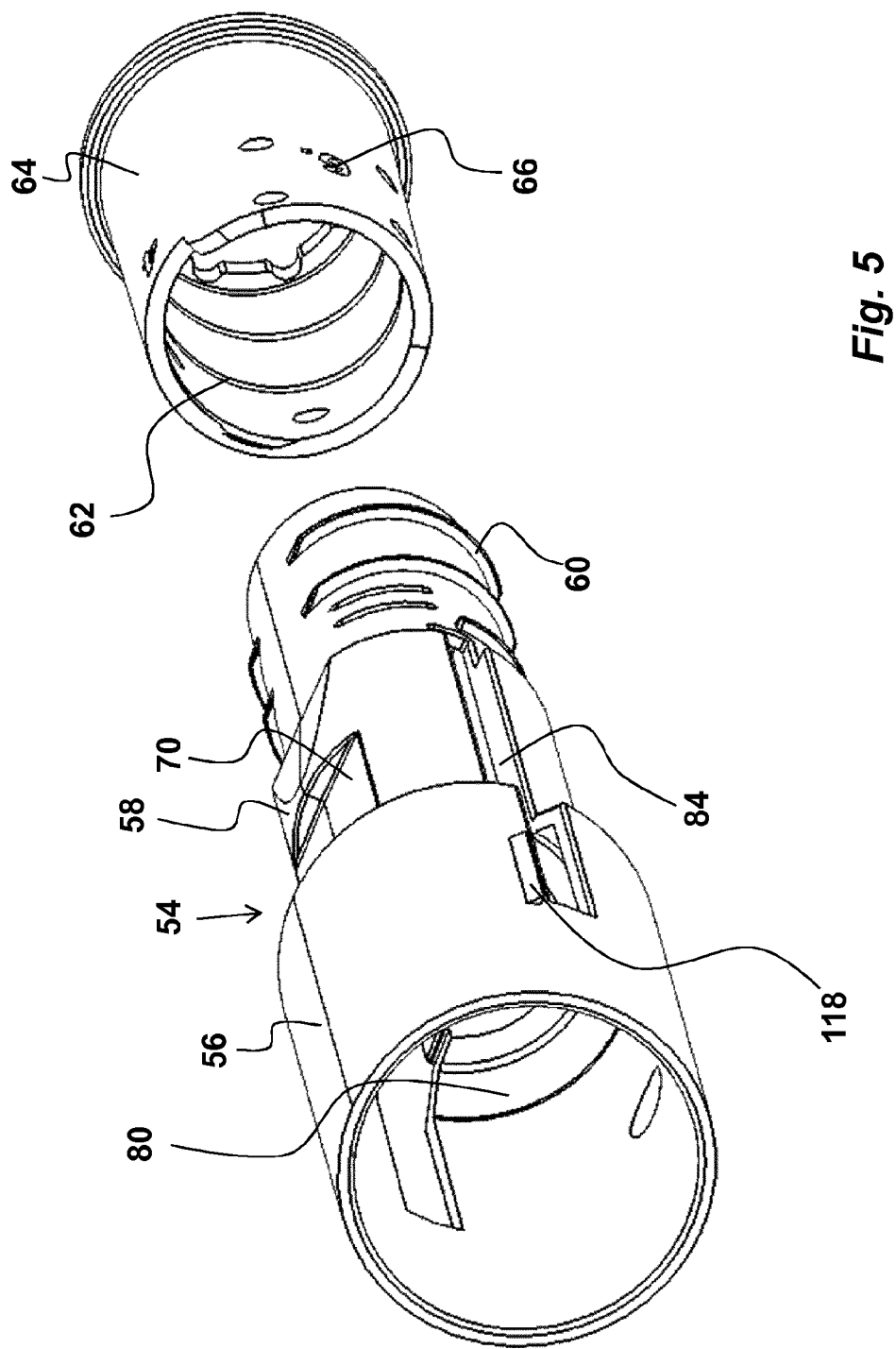

Surrounding the medicament container holder 24 and coaxial therewith is a medicament delivery member cover 54, FIG. 5. The medicament delivery member cover 54 is arranged with a distal tubular part 56, which transforms into a proximal tubular part 58, FIG. 5. In this respect, the inner diameter of the proximal tubular part 58 is somewhat larger than the outer diameter of the medicament container holder 24. Further, the outer diameter of the proximal tubular part 58 is somewhat smaller than the second tubular part 16*b* of the proximal housing part 16 such that the medicament delivery member cover 54 can move in the longitudinal direction in relation to the proximal housing part 16. The medicament delivery member cover 54 is thus resiliently movable in relation to the proximal housing part 16 between an extended position where a proximal tubular portion of the medicament delivery member cover 54 protrudes from the transversal proximal end of the proximal housing part 16, and a retracted position where the transversal proximal end of the proximal tubular portion of the medicament delivery member cover 54 is flush with the proximal transversal end of the proximal housing part 16.

Figure 6:
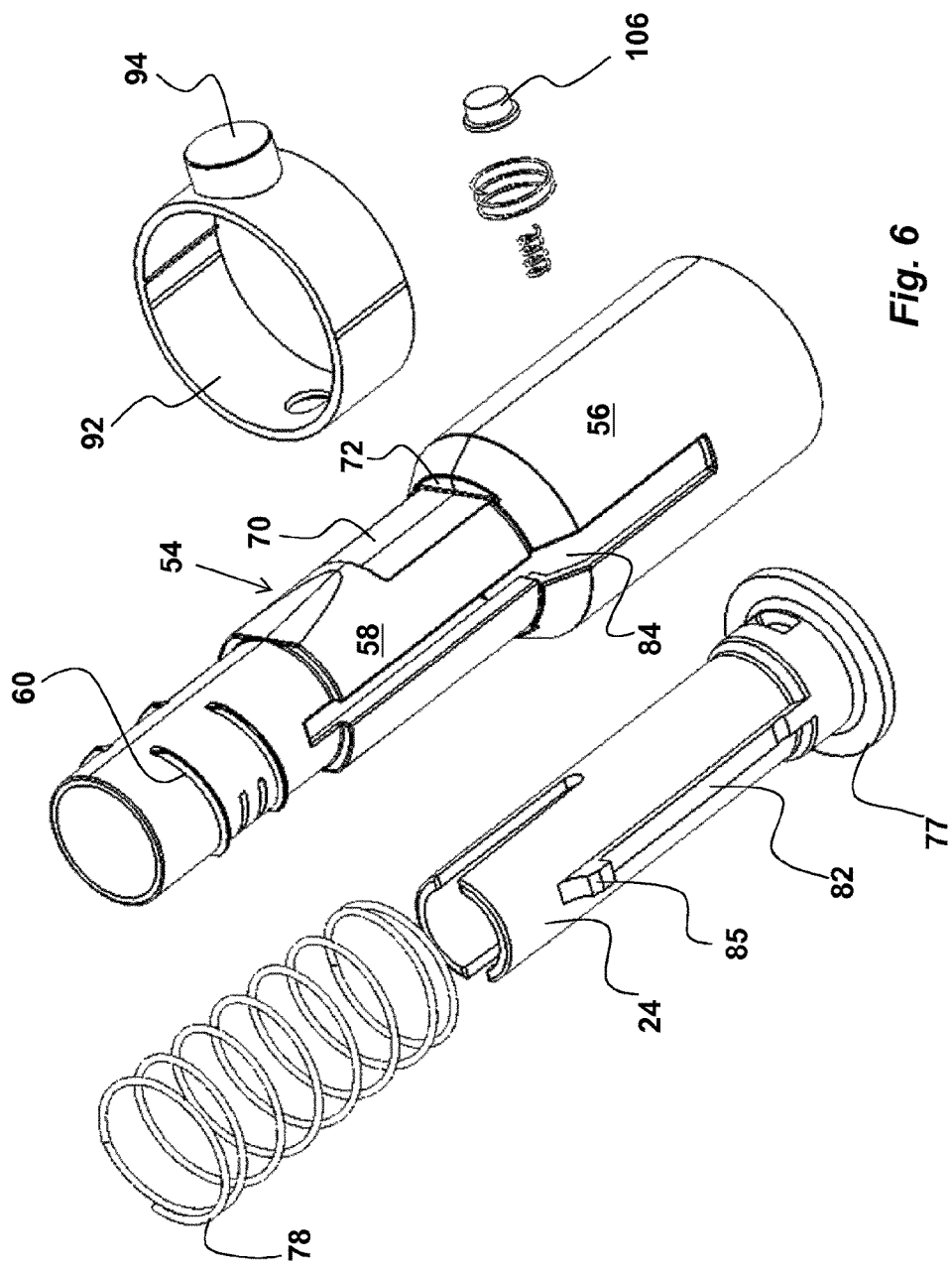

An outer surface of the medicament delivery member cover 54 is arranged with threads 60, FIGS. 5 and 6, which threads 60 are arranged to cooperate with corresponding threads 62, FIG. 5, on an inner surface of a generally tubular element 64, hereafter named depth adjuster. The outer surface of the depth adjuster 64 is arranged with indicia 66, such as numbers. These indicia are to cooperate with a cut-out 68, FIGS. 1 and 2, in the proximal end of the second tubular part 16*b*, FIG. 1.

Figure 7:
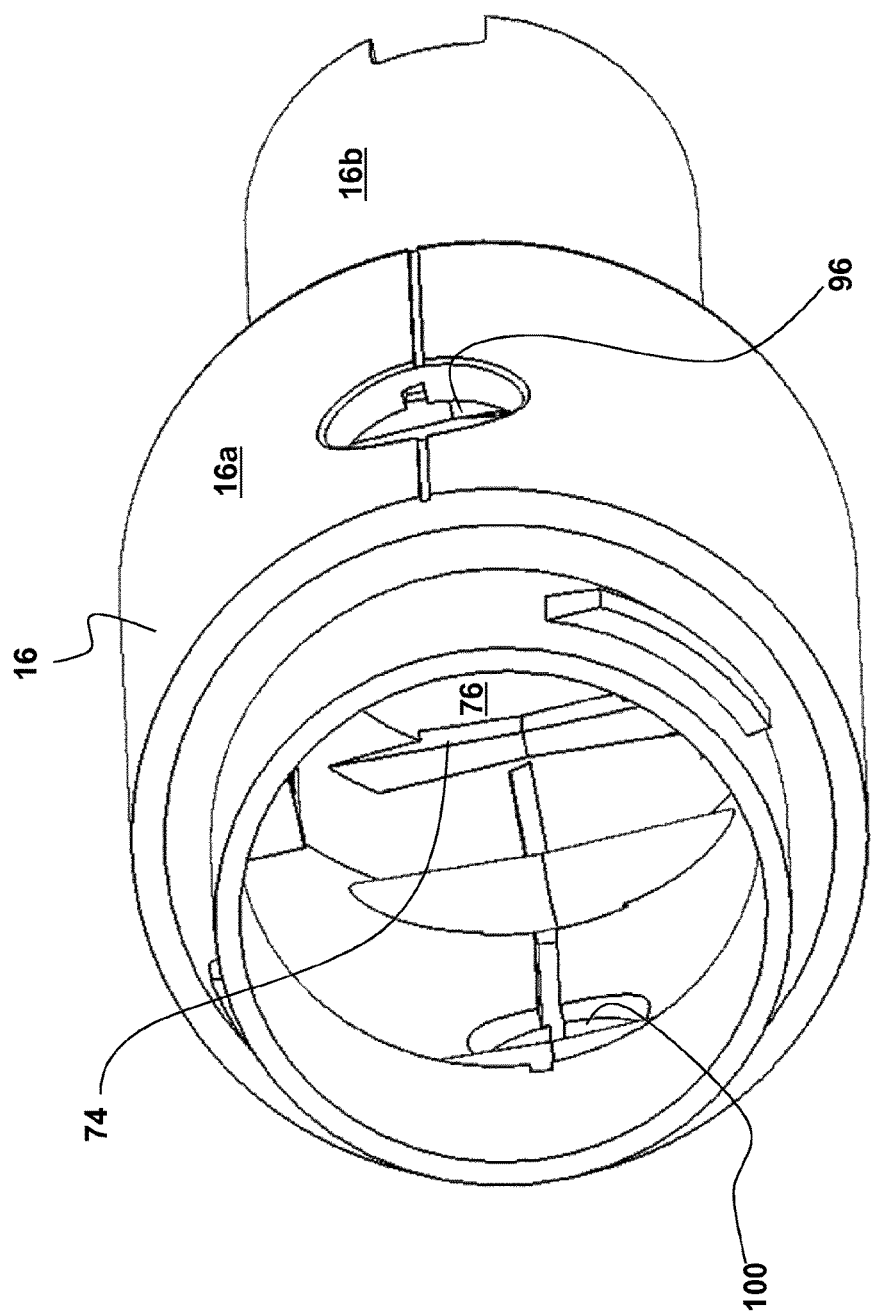

The medicament delivery member cover 54 is further arranged two flat areas 70, FIGS. 5 and 6, on its outer surface, where the areas are positioned opposite each other. The flat areas 70 create proximally directed transversal ledges 72, FIG. 6. The inner surface of the proximal housing part 16 is further arranged with two straight sections 74, FIG. 7, of a central passage 76, and is arranged to cooperate with the flats areas 70 such that a rotational lock is obtained between the components while allowing longitudinal movement relative each other. The transversal ledges 72 also functions as movement limiters when they are brought in contact with the straight sections 74 of the proximal housing part 16.

The medicament container holder 24 is further arranged with a circumferential outwardly extending ledge 77 at its distal area, FIG. 6. A medicament delivery member return force element 78, in the embodiment shown arranged as a compression spring, is arranged between a proximally directed surface of the ledge 77 and a distally directed circumferential ledge 80 of the medicament delivery member cover, FIG. 5, wherein the medicament delivery member return force element 78 urges the medicament container holder 24 and the medicament container 18 in the distal direction. The medicament holder 24 is also arranged with an outwardly directed ledge 82 on its outer surface, FIG. 6, which ledge 82 is intended to fit into a longitudinally extending groove 84 in the medicament delivery member cover 54 for guide purposes. Further the proximal end of the ledge 82 is arranged with an outwardly directed protrusion 85.

Figure 8:
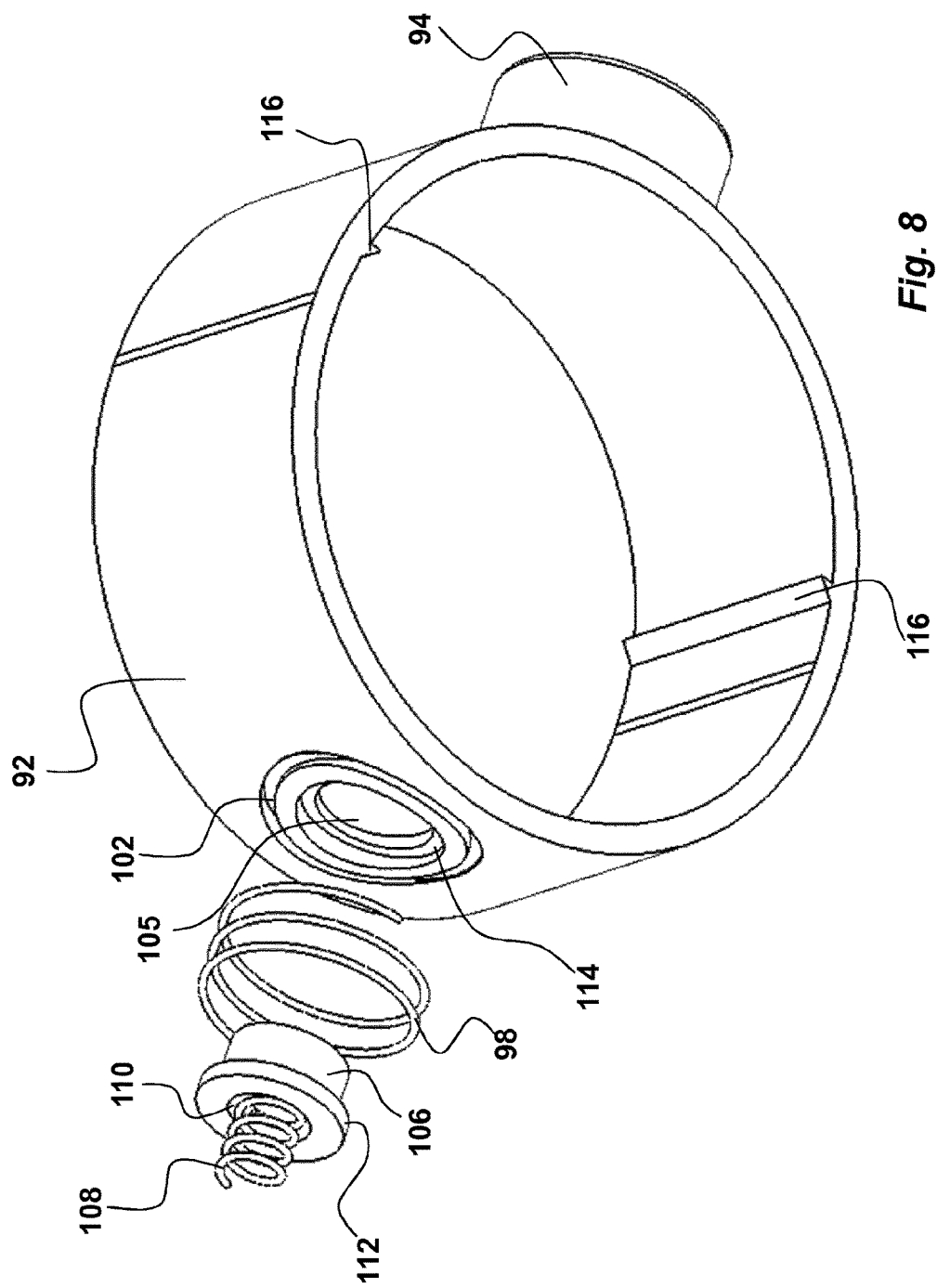

According to the embodiment shown, the device is arranged with a medicament delivery member cover locking mechanism 90, FIG. 2. It comprises in the embodiment shown a manually operated actuator 92 comprising a generally tubular or ring-shaped body, FIGS. 6 and 8, placed inside the proximal housing part 16. The actuator 92 is provided with a radially outwardly extending protrusion or button 94 comprised in the actuator, which button 94 is fitted into a passage 96, FIG. 7, in the proximal housing part 16, whereby the button 94 extends through the passage 96 such that it may function as a manually operated actuator, accessible to the user. On the opposite side of the actuator, as seen from the button 94, a first resilient force element 98 is arranged, in the embodiment shown a compressions spring 98, FIG. 8. Preferably the first resilient force element 98 is held in position in that one end is placed in a seat 100 on the inner surface of the proximal housing part 16, FIG. 7, while the other end is placed in a seat 102 on the outer surface of the actuator 92, FIG. 8. Further, a hole or passage 105, FIG. 8, is arranged in the actuator 92 coaxial with the seat 102 of the first resilient force element 98. A first lock member 106 in the form of a circular cap is fitted onto the passage 105 in the embodiment shown, and is held in place by a second resilient force element 108, in the embodiment shown as a compression spring arranged in a seat 110 of the first lock member 106 and the inner surface of the proximal housing part. The first lock member 106 is further arranged with a circumferential ledge 112, which ledge 112 is arranged to fit into a circumferential groove 114 of the passage 105 such that the movement inwards of the first lock member 106 in the radial direction is limited. Thus, the first lock member 106 and the actuator 92 are movable in relation to each other, more particularly in a radial direction. The first lock member 106 is configured such that it may extend through the passage 105 of the actuator 92 and through a second lock member 104 i.e. a passage on the medicament delivery member cover 54 when the medicament delivery member cover 54 is in the extended position. On an inner surface of the actuator 92, first actuation locking members 116 are arranged, in the embodiment shown as two first ledges, extending in the longitudinal direction of the device. The first ledges have a wedge-shaped cross-section. These first actuation locking members 116 are intended to cooperate with second actuation locking members 118 comprised on the outer surface of the medicament delivery member cover 54, at the distal part thereof, as seen in FIG. 5. The second actuation locking members 118 are arranged, in the embodiment shown, as two second ledges extending in the longitudinal direction. These second ledges also have a wedge-shaped cross-section arranged to operably connect with the first actuation locking members 116.

The device further comprises a delivery member shield remover (not shown) arranged to connect with a delivery member shield (not shown), wherein said needle shield remover is arranged to be removably inserted into a proximal end of the proximal housing part 16 through medicament delivery member cover 54 and wherein the delivery member shield remover, when inserted into the proximal end of the proximal housing part 16 is adapted to be used to interact with the reloadable drive mechanism 26 accommodated in said distal housing part 15 such that a user can relocate the reloadable drive mechanism 26 from said proximal or extended position to said distal or cocked position. In other words, when the proximal housing part 16 is disconnected from the distal housing part 15 and the delivery member shield remover is positioned into the proximal end of the proximal housing part 16, the proximal end of the delivery member shield remover is inserted through the proximal end of the distal housing part 15 such that the proximal end of the the delivery member shield remover abuts with the reloadable drive mechanism 26 accommodated in said distal housing part 15 and by holding the distal housing part fixed and exerting a pressure on the proximal housing part 16 such that the proximal housing part 16 moves along the longitudinal axis (L) in relation to the fixed distal housing part, the reloadable drive mechanism 26 is relocated from said proximal or extended position to said distal or cocked position.

Figure 9:
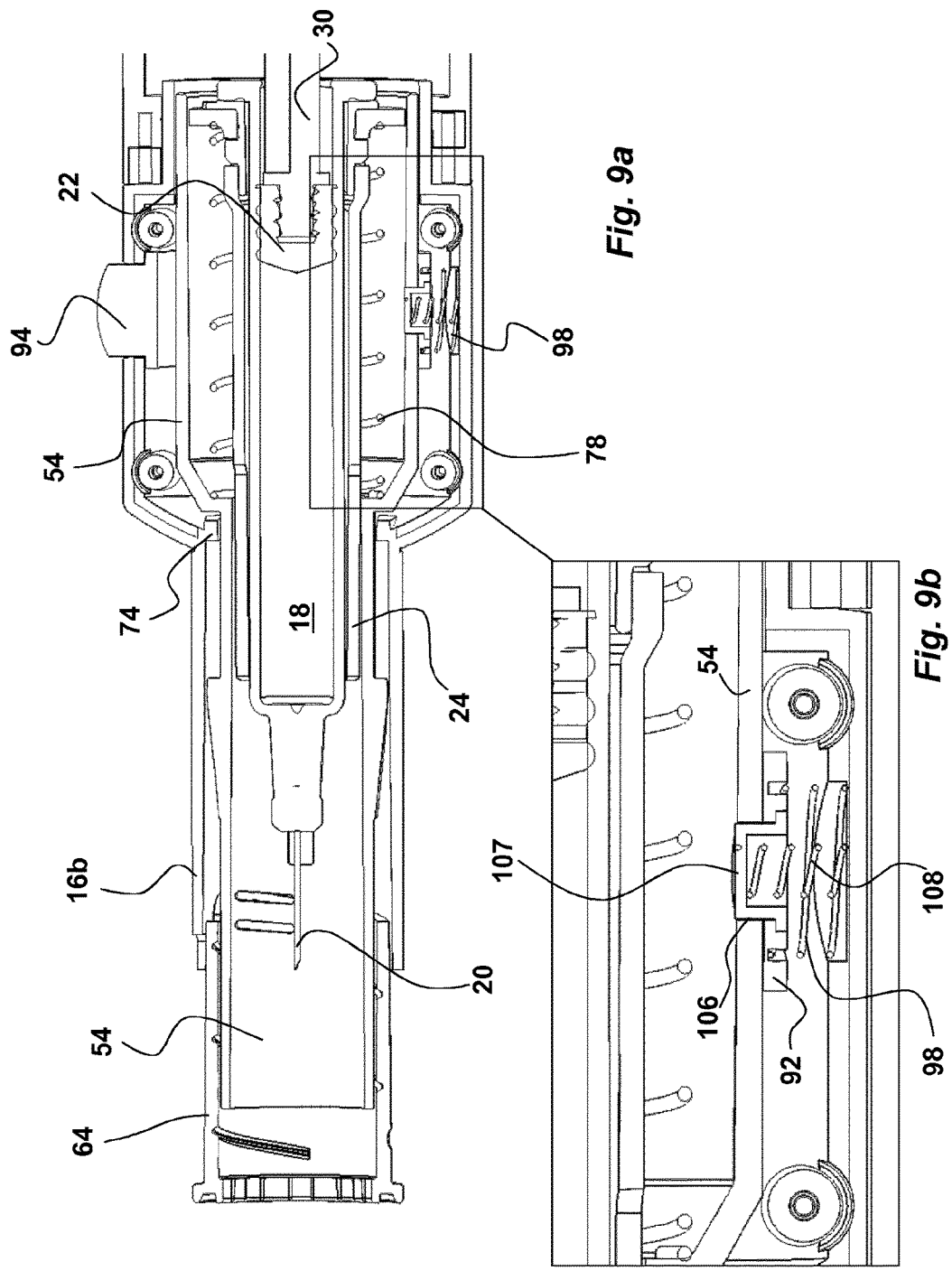
Figure 10:
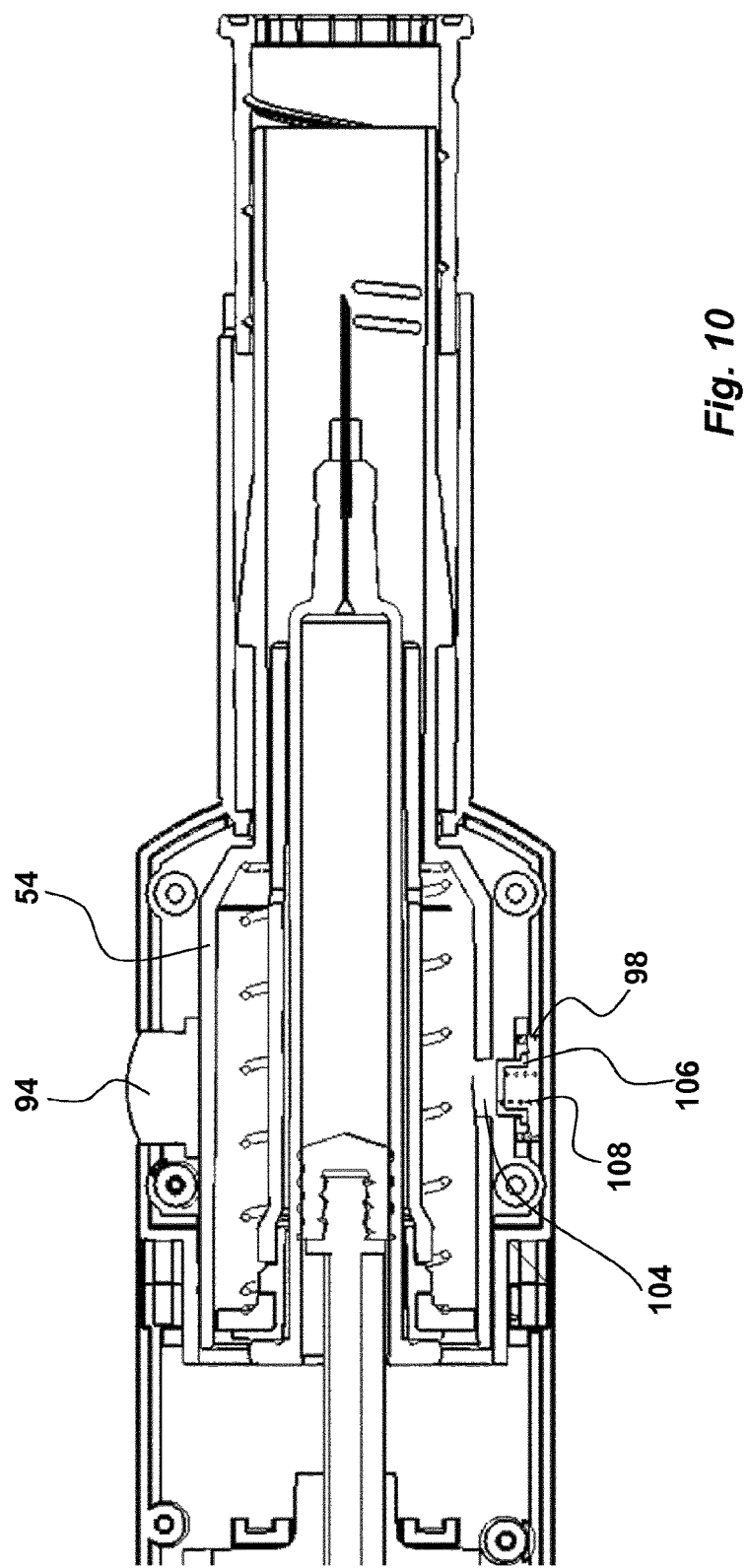

The device according to the invention is arranged to function as follows. When the device is delivered to the user, the medicament delivery member cover 54 is in the extended position, FIG. 9a. The reloadable drive mechanism is in the cocked state where the drive spring 32 is compressed as seen in FIG. 3. The medicament delivery member cover 54 is locked by the medicament delivery member cover locking mechanism 90 in that the actuator 92 is forced in a radial direction, i.e. in a direction generally transversal to the longitudinal axis (L), by the first resilient force element 98, FIG. 9b. Also the first lock member 106 is forced in the same direction i.e. transversal to the longitudinal axis (L), by the second resilient force element 108, whereby the first lock member 106 is positioned inside the second lock member 104 i.e. the passage, FIG. 10. The first lock member 106 thus blocks any movement in the longitudinal direction of the medicament delivery member cover 54.

In order to activate the device for delivery of the medicament, the user presses on the button 94 of the actuator 92 of the medicament delivery member locking mechanism 90 in the radial direction opposite the force direction of the first resilient force element 98 and the second resilient force element 108. This movement of the button 94 and thus the actuator 92 of the medicament delivery member cover locking mechanism 90 will cause the first lock member 106 to be moved out of the second lock member 104 of the medicament delivery member cover 54, FIG. 10, wherein a transversal surface 107 of the first lock member 106 is flush with the inner surface of the actuator 92. The first 116 and second 118 actuation locking members will now engage and hold the actuator 92 in the actual position.

Figure 11:
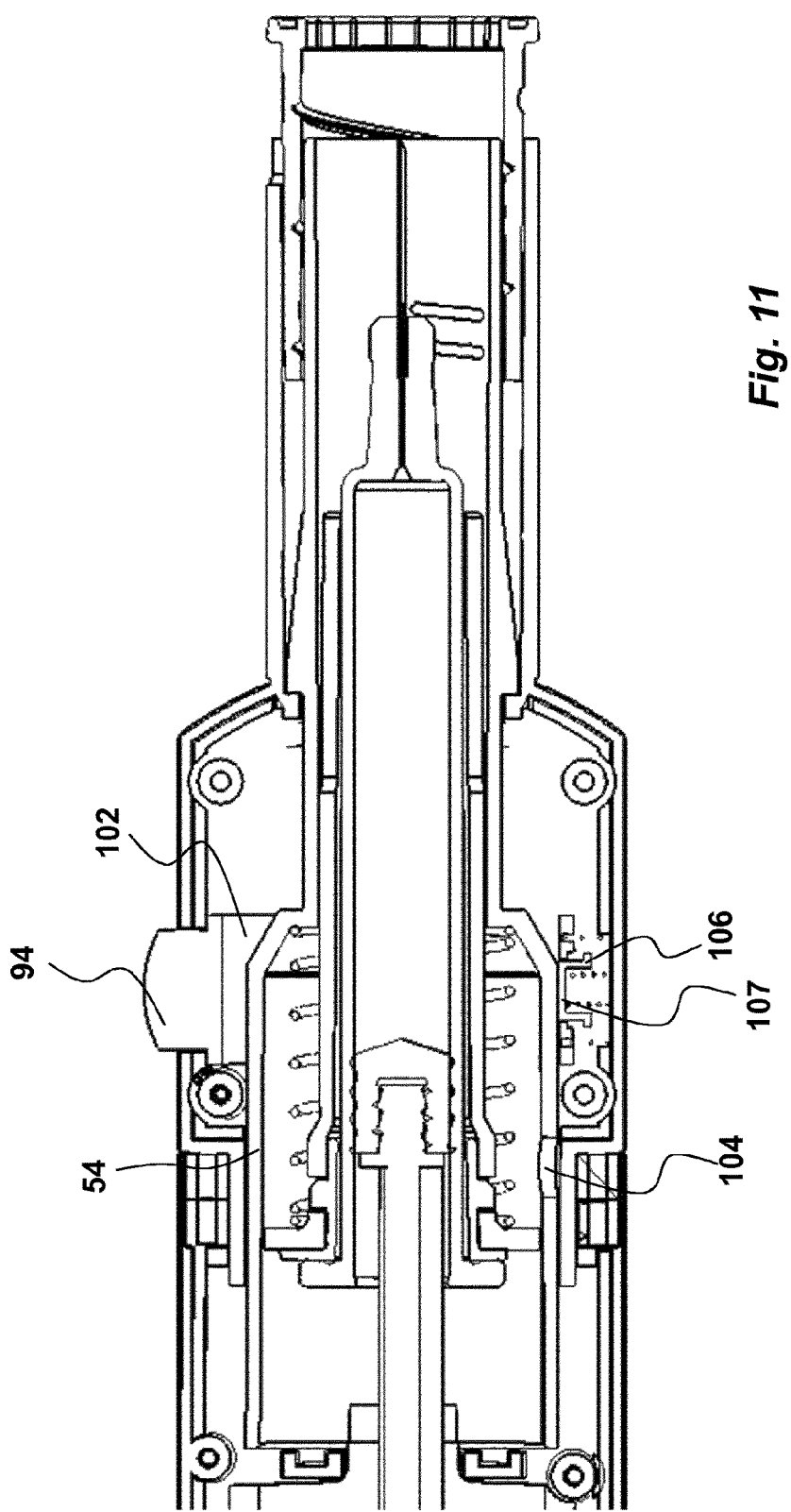

The device is now activated in that the medicament delivery member cover 54 can be moved i.e. pressed against a dose delivery site such that the medicament delivery member cover 54 is moved from the extended to the retracted position. The user then presses a proximal end of the medicament delivery member cover 54 against the dose delivery site, whereby the medicament delivery member cover 54 is moved in the distal direction inside the housing of the device, FIG. 11. Upon pressing the device against the dose delivery site, the distal part of the medicament delivery member cover 54 comes into contact with the proximally directed end surfaces 52 of the arms 48 of the blocking element 46, FIG. 4. Thus the blocking element 46 is moved out of blocking position, allowing the release mechanism 34 to be activated. As soon as the medicament delivery member cover 54 is moved from the extended position to the retracted position, the first 116 and second 118 actuation locking members are disengaged and the first resilient force element 98 forces the actuator 92 to move such that the button 94 protrudes through the passage 96 on said housing 10 while the first lock member 106, more particularly, the transversal surface 107 of the first lock member 106 is abutting on the peripheral surface of the distal tubular part of medicament delivery member cover 54 as seen in FIG. 11. The next step is then for the user to activate the dose delivery sequence.

According to the embodiment of FIGS. 1-11, the user depresses the trigger button 38 of the release mechanism 34, whereby the drive spring 32 is released in that the reloadable drive mechanism locking element 40 is moved out of contact with the plunger rod driver 28. The plunger rod driver 28 and the drive spring 32 then act to force the plunger rod 30 in the proximal direction acting on the stopper 22 inside the medicament container 18. Since the medicament is incompressible and the passage through the medicament delivery member is narrow, the medicament container holder 24 with the medicament container 18 will be moved towards the proximal direction in relation to the housing, against the rather weak force of the medicament delivery member return force member 78. The movement of the medicament container 18 will now cause a penetration of the medicament delivery member 20 into the skin of the user. The force of the drive spring 32 is far more powerful than that of the medicament delivery member return force element 78, which therefore is compressed when the reloadable drive mechanism 26 is released. The penetration movement is stopped when the circumferential ledge 77 of the distal end of the medicament container holder is adjacent the distally directed stop ledge 80 of the medicament delivery member cover with the fully compressed medicament delivery member return force element 78 between the ledges.

The force of the drive spring 32 now forces the plunger rod 30 in the proximal direction in relation to the medicament container 18, moving the stopper 22 in the proximal direction, whereby a dose of medicament is delivered into the body of the user. When the stopper has reached its proximal end position, the dose delivery sequence has ended and the user may remove the device from the dose delivery site. Since the force on the medicament delivery member cover 54 now is removed at its proximal end, the medicament delivery member return force member 78 will force the medicament delivery member cover 54 in the proximal direction form the retracted position to the extended position, whereby the medicament delivery member 20 is shielded by the medicament delivery member cover 54. When the medicament delivery member cover 54 is returned to the extended position, the second resilient force member 108 forces the first lock member 106 to be moved into the second lock member 104 i.e. the passage on the medicament delivery member cover 54 such that the medicament delivery member cover 54 is locked again by the medicament delivery member cover locking mechanism 90.

Figure 12:
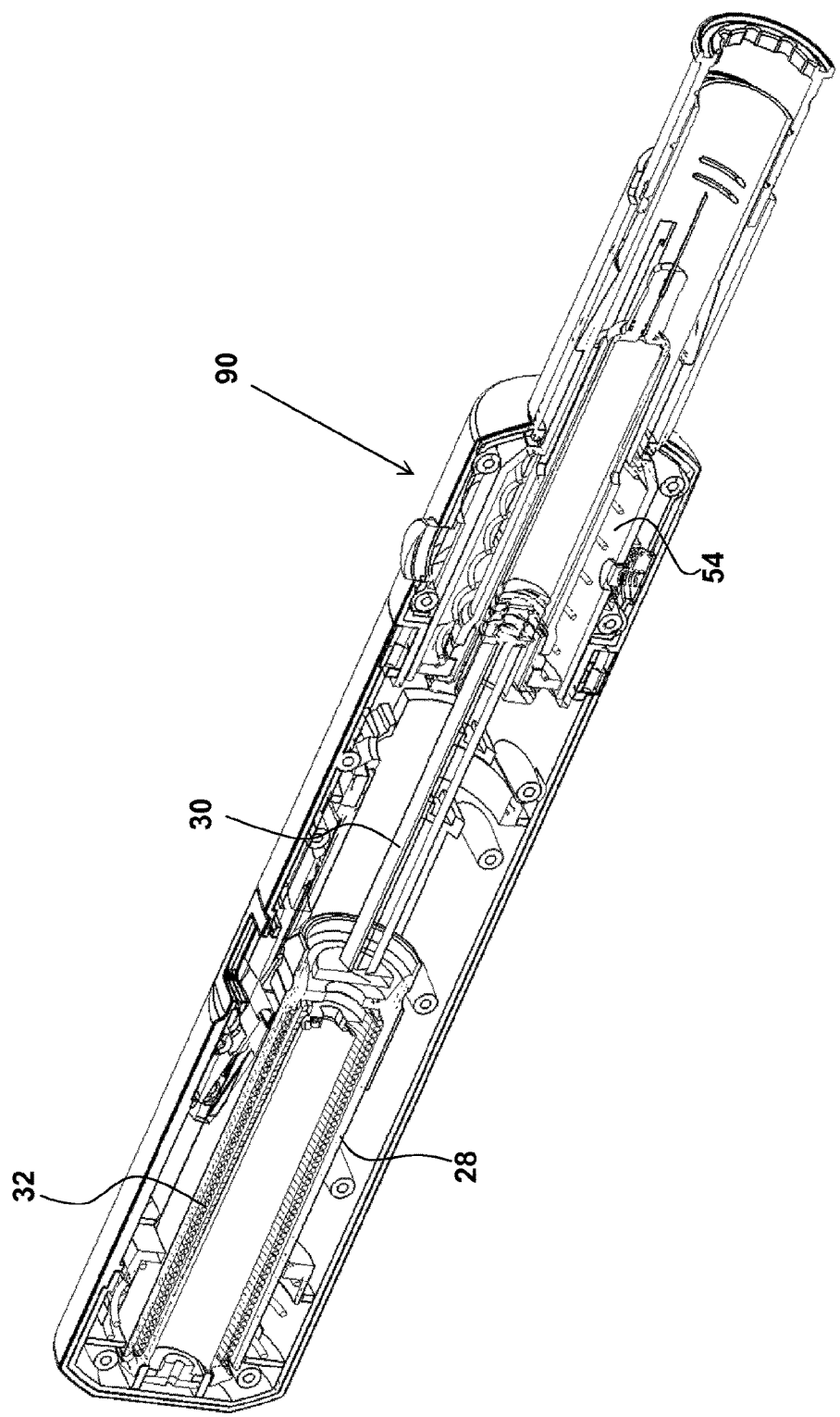
FIGS. 12-13 shows a variant of the embodiment of FIG. 1.
Figure 13:
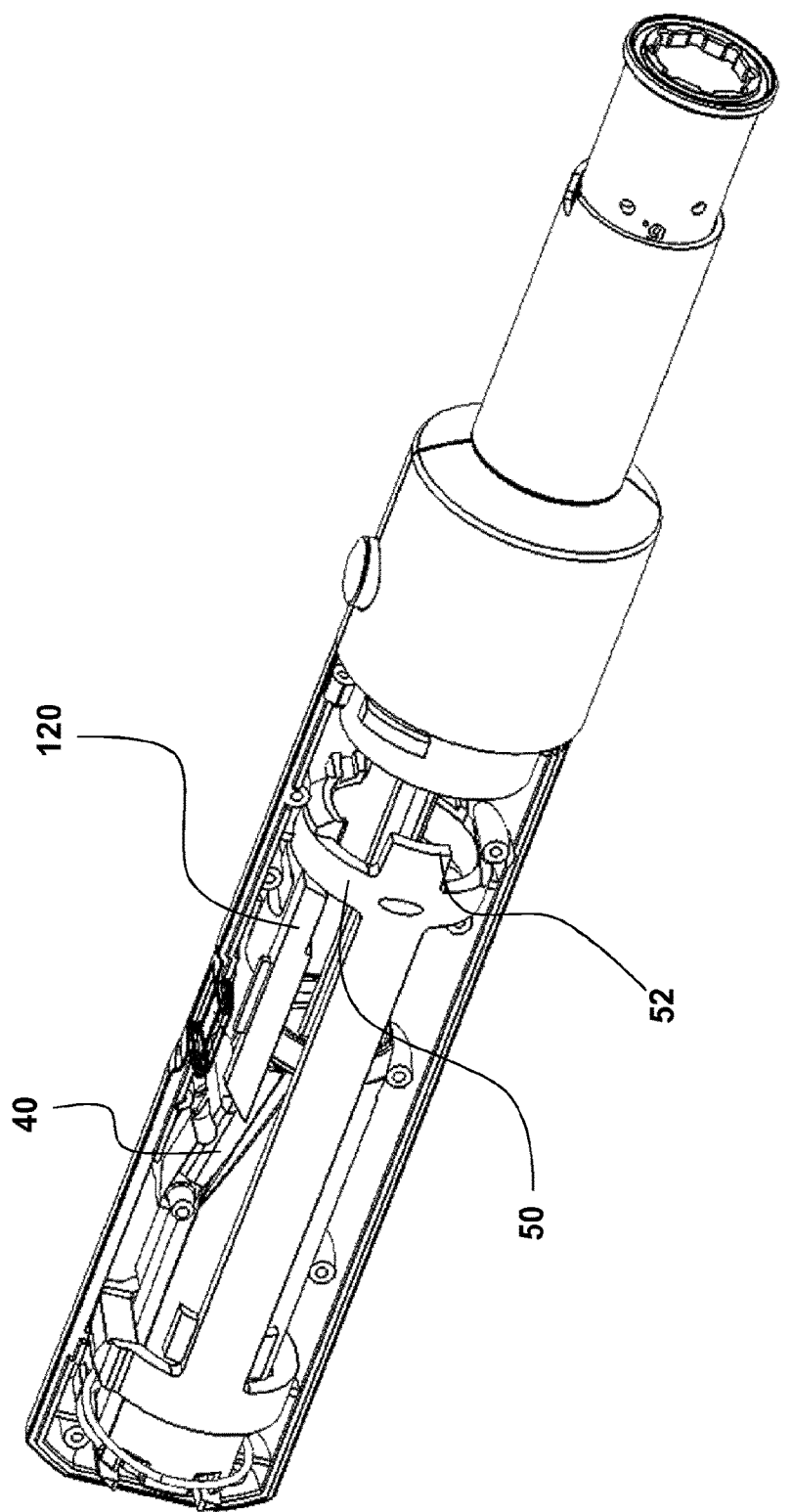

FIGS. 12 and 13 show a modified embodiment of the medicament delivery device, where the same components have been given the same reference numerals. Here the manually operated release mechanism 34 has been removed in order to simplify the handling of the device.

The activation of the device of FIGS. 12 to 13 is performed in the same manner as described above by manually operating the medicament delivery member cover locking mechanism 90 such that the medicament delivery member cover is released. The medicament delivery member cover is now pressed against the dose delivery site, whereby the medicament delivery member cover is moved distally inside the housing of the device. The movement will cause the distally directed end surface of the medicament delivery member cover to come in contact with the proximally directed end surfaces of the 52 of the arms 48 of the blocking element 46, whereby the arms 48 are also moved in the distal direction. This will also cause the second ring-shaped element 50 to move in the distal direction until it comes in contact with the reloadable drive mechanism locking element 40.

A release mechanism, in the embodiment shown arranged as a movement transfer element 120, FIG. 13, is arranged between a distally directed surface of the second ring-shaped element 50 and the reloadable drive mechanism locking element 40, such that the transfer element 120 of the reloadable drive mechanism will also move in the distal direction and will in turn cause the reloadable drive mechanism locking element 40 to be moved out of contact with the plunger rod driver 28, which causes a movement of the plunger rod driver 28 and the plunger rod 30 in the proximal direction for a penetration sequence and a subsequent injection sequence as described above.

It is to be understood that the the reloadable drive mechanism can in a simple and reliable manner be reloaded It is to be understood that the elements and mechanisms described above and shown in the drawings are only examples of structures that may be replaced by other elements and/or mechanisms displaying the same or similar function for obtaining the desired end result. Further it is to be understood that the embodiment described above and shown in the drawings only is to be regarded as comprising a non-limiting example of the invention and that it may be modified in many ways within the scope of the patent claims.

The invention claimed is:

1. A medicament delivery device, comprising:
   a generally elongated housing having a distal end and a proximal end along a longitudinal axis, the housing being arranged to accommodate a medicament container enclosing a medicament and a medicament delivery member connected to an accommodated medicament container;
   a reloadable drive mechanism configured to act, upon activation, on the accommodated medicament container;
   a medicament delivery member cover operably arranged at the proximal end and slidable in relation to the housing along the longitudinal axis between an extended position in which said medicament deliver member is covered and a retracted position in which said medicament delivery member is enclosed; and
   a medicament delivery member cover lock mechanism, comprising:
     a first lock member provided on an actuator that is movably arranged in relation to the housing; and
     a second lock member provided on the medicament delivery member cover;
   wherein the first lock member is operable to engage the second lock member for blocking movement of the medicament delivery member cover at said extended position; and
   the actuator is movable in a direction generally transversal to the longitudinal axis (L) in relation to the medicament delivery member cover such that manual actuation of the actuator in a direction generally transverse to the longitudinal axis causes the first lock member to be moved out of engagement with the second lock member, thereby allowing the medicament delivery member cover to be moved to the retracted position.

2. The medicament delivery device of claim 1, wherein the first lock member is movable in relation to the actuator.

3. The medicament delivery device of claim 1, wherein the actuator coaxially surrounds the medicament delivery member cover.

4. The medicament delivery device of claim 3, wherein the actuator further comprises a button that protrudes through a passage on the housing for manual operation.

5. The medicament delivery device of claim 4, wherein the medicament delivery member cover lock mechanism further comprises a first resilient force member operably arranged to urge the actuator in the direction generally transverse to the longitudinal axis.

6. The medicament delivery device of claim 5, wherein the medicament delivery member cover lock mechanism further comprises a second resilient force member operably arranged to urge the first lock member in the direction generally transverse to the longitudinal axis.

7. The medicament delivery device of claim 1, wherein the first lock member comprises a cap arranged to protrude through a first passage on the actuator, and the second lock member comprises a second passage in which the cap fits.

8. The medicament delivery device of claim 1, wherein the medicament delivery member cover lock mechanism further comprises:
- a first actuation locking member provided on the actuator; and
- a second actuation locking member provided on the medicament delivery member cover;
- wherein the first actuation locking member is operably engageable with the second actuation locking member for blocking movement of the actuator in the direction generally transverse to the longitudinal axis after the actuator is manually activated, whereby the medicament delivery member cover is allowed to be moved.

9. The medicament delivery device of claim 1, further comprising:
- a reloadable drive mechanism locking element configured to lock the reloadable drive mechanism in a cocked state;
- a manually operable release mechanism operably arranged to act, upon operation, on the reloadable drive mechanism locking element for releasing the reloadable drive mechanism; and
- a blocking element operably engageable with the manually operable release mechanism and releasably connected to the medicament delivery member cover;
- wherein movement of the medicament delivery member cover in a distal direction causes the blocking element to move out of blocking engagement with the manually operable release mechanism, whereby the manually operable release mechanism is free to be manually operated for activating dose delivery.

10. The medicament delivery device of claim 9, wherein the manually operable release mechanism comprises a trigger button operably arranged on the housing and configured to interact with the reloadable drive mechanism.

11. The medicament delivery device of claim 9, wherein the reloadable drive mechanism comprises:
- a plunger rod driver that is axially movable within the housing between a distal end position and a proximal end position; and
- a drive spring configured to bias the plunger rod driver toward the proximal end position.

12. The medicament delivery device of claim 11, further comprising the reloadable drive mechanism locking element configured to interact with the plunger rod driver to hold the plunger rod driver with the drive spring in a distal position.

13. The medicament delivery device of claim 12, wherein the plunger rod driver is coupled to a stopper positioned inside the accommodated medicament container.

14. The medicament delivery device of claim 1, further comprising:
- a reloadable drive mechanism locking element configured to lock the reloadable drive mechanism in a cocked state; and
- a release mechanism operably arranged to act, upon operation, on the reloadable drive mechanism locking element for releasing the reloadable drive mechanism;
- wherein movement of the medicament delivery member cover in a distal direction causes the release mechanism to act on the reloadable drive mechanism locking element for activating dose delivery.

* * * * *